(12) United States Patent
Diamant

(10) Patent No.: US 9,993,314 B2
(45) Date of Patent: Jun. 12, 2018

(54) ORTHODONTIC BRACKET

(71) Applicant: Cerna Diamant, Rishon Lezion (IL)

(72) Inventor: Cerna Diamant, Rishon Lezion (IL)

(73) Assignee: Cerna Diamant, Rishon LeZion (IL)

( * ) Notice: Subject to any disclaimer, the term of this patent is extended or adjusted under 35 U.S.C. 154(b) by 0 days. days.

(21) Appl. No.: 15/559,894

(22) PCT Filed: Feb. 9, 2016

(86) PCT No.: PCT/IL2016/050157
§ 371 (c)(1),
(2) Date: Sep. 20, 2017

(87) PCT Pub. No.: WO2016/151569
PCT Pub. Date: Sep. 29, 2016

(65) Prior Publication Data
US 2018/0055601 A1    Mar. 1, 2018

(30) Foreign Application Priority Data
Mar. 23, 2015   (IL) .......................... 237908

(51) Int. Cl.
*A61C 7/00*    (2006.01)
*A61C 7/14*    (2006.01)

(52) U.S. Cl.
CPC ............... *A61C 7/006* (2013.01); *A61C 7/14* (2013.01)

(58) Field of Classification Search
CPC .................................. A61C 7/006; A61C 7/14
See application file for complete search history.

(56) References Cited

U.S. PATENT DOCUMENTS

| 4,017,973 A * | 4/1977 | Nelson ................... A61C 7/006 433/18 |
| 4,396,373 A | 8/1983 | Dellinger |
| 4,457,707 A | 7/1984 | Smiley et al. |
| 4,565,526 A | 1/1986 | Kawata et al. |

(Continued)

FOREIGN PATENT DOCUMENTS

| JP | 2005237658 A | 9/2005 |
| KR | 20100022678 A | 3/2010 |

OTHER PUBLICATIONS

"International Application No. PCT/IL2016/050157, International Search Report dated Jun. 6, 2016", (dated Jun. 6, 2016), 3 pgs.

(Continued)

*Primary Examiner* — Nicholas Lucchesi
(74) *Attorney, Agent, or Firm* — FisherBroyles, LLP; Ariel Reinitz

(57) ABSTRACT

In one aspect, the present invention is directed to an orthodontic bracket, comprising: a vertical bore; a bendable drop-in hook threaded into the vertical bore; and an annular magnetic object, in which the drop-in hook is threaded into. In another aspect, the present invention is directed to an orthodontic braces arrangement, comprising: at least two distant brackets, each installed on a different jaw of a user; and each of the distant brackets having at least one annular magnetic object secured thereto by a bendable drop-in hook; wherein a distance between magnetic objects of one bracket and another bracket is less than 2 mm; thereby providing intermaxillary attraction or propulsion force, depending on a polarity orientation of the magnetic objects.

20 Claims, 6 Drawing Sheets

(56) References Cited

U.S. PATENT DOCUMENTS

| | | | | |
|---|---|---|---|---|
| 4,869,667 A * | 9/1989 | Vardimon | ............... | A61C 7/006 |
| | | | | 433/18 |
| 5,205,736 A * | 4/1993 | Blechman | ............... | A61C 7/006 |
| | | | | 433/18 |
| 5,334,015 A * | 8/1994 | Blechman | ............... | A61C 7/006 |
| | | | | 433/18 |
| 6,062,855 A * | 5/2000 | Karlin | .................... | A61C 7/006 |
| | | | | 433/20 |
| 6,217,324 B1 * | 4/2001 | Kesling | .................... | A61C 7/00 |
| | | | | 433/14 |
| 9,498,302 B1 * | 11/2016 | Patel | ....................... | A61C 7/006 |
| 2004/0180307 A1 * | 9/2004 | Graham | ................. | A61C 17/16 |
| | | | | 433/118 |
| 2015/0238281 A1 * | 8/2015 | Alauddin | ............... | A61C 7/006 |
| | | | | 433/11 |

OTHER PUBLICATIONS

"International Application No. PCT/IL2016/050157, Written Opinion dated Jun. 6, 2016", (dated Jun. 6, 2016), 5 pgs.

* cited by examiner

ORTHODONTIC BRACKET

PRIORITY APPLICATIONS

This application is a U.S. National Stage Filing under 35 U.S.C. 371 from International Application No. PCT/IL2016/050157, filed on 9 Feb. 2016, and published as WO2016/151569 on 29 Sep. 2016, which claims the benefit of priority to Israeli Application No. 237908, filed on 23 Mar. 2015; which applications and publication are incorporated herein by reference in their entirety.

TECHNICAL FIELD

The present invention relates to the field of dental braces. More particularly, the invention relates to an orthodontic bracket, and an orthodontic braces arrangement.

BACKGROUND ART

"Dental braces (also known as orthodontic braces, or braces) are devices used in orthodontics that align and straighten teeth and help to position them with regard to a person's bite, while also working to improve dental health. They are often used to correct underbites, as well as mal-occlusions, overbites, cross bites, open bites, deep bites, crooked teeth, and various other flaws of the teeth and jaw. Braces can be either cosmetic or structural. Dental braces are often used in conjunction with other orthodontic appliances to help widen the palate or jaws and to otherwise assist in shaping the teeth and jaws." (From Wikipedia)

The device puts pressure on a user's teeth. As a result of applying braces over time, usually months, the teeth of a user displace as a response to the pressure direction. Orthodontics takes advantage of this fact for both, improving the bite of a user, and also the aesthetic appearance of his face.

The most basic form of dental braces is orthodontic braces.

FIG. 1 pictorially illustrates orthodontic braces, according to the prior art.

In the figure is shown two sets of orthodontic braces: orthodontic braces 10a is applied on the teeth of upper jaw 28a, and orthodontic braces 10b is applied on the teeth of the lower jaw 28b. The application of braces displaces the teeth 16 as a result of exerting pressure thereon.

A typical structure of orthodontic braces comprises, for each jaw, an arch wire 14 threaded through brackets 12. The brackets are attached to the teeth 16 of a user, e.g., by gluing.

As the arch wire exerts pressure on the brackets and teeth, the teeth are displaced in a process over several months.

The teeth can be displaced in different ways. For example, spring 18 is used to put additional force on adjacent teeth, whether in attraction or propulsion. The teeth are pushed or pulled from each other according to the orientation of the force applied by the spring—pulling or pushing force.

As illustrated, each of the elastic rubber bands 20 is connected to anchoring points of different jaws. The anchoring points may be attached to the brackets 12, or to the arch wire 14 using arch wire hook 22, which is secured to the arch wire 14.

By exerting force between different jaws, the teeth of one jaw are displaced with reference to the other. The active force is the horizontal vector of the pulling force of each of the elastic rubber bands 20. Such a process requires months.

In order to anchor an elastic rubber band 20 to bracket 12, the bracket is coupled with an anchoring element, which may be in form of:

(a) Arch wire hook 22, which is secured to the arch wire 14 (and also known as a Crimpable hook);
(b) Bracket hook 24, which is attached to bracket 12;
(c) Bracket loop (not illustrated) which is a loop attached to an arch wire or bracket (also known as a K hook).
(d) Drop-in hook 34 (illustrated in FIG. 2).

FIG. 2 schematically illustrates an additional anchoring element of the prior art.

The anchoring element is known as a drop-in hook, and is marked herein by reference numeral 34.

In order to connect a drop-in hook to bracket 12, the bracket comprises a vertical bore 32. The bore is illustrated in FIG. 2 in dashed lines, as it is hidden.

The end 34' of the drop-in hook 34 is bent, in order to prevent the drop-in hook from being pulled out of the bracket. The bending operation is carried out after the straight drop-in hook is inserted into the bracket's bore 32 and threaded/secured therein.

The drop-in hook may be inserted into bore 32 upside-down, and also inserted upside-up.

As illustrated in FIG. 1, the elastic rubber bands 20 generate an obstacle during the process of eating. Furthermore, in addition to the obstacle of an eating process, elastic rubber bands cause a grave aesthetic fault. As a result, some users may avoid using teeth braces, and prefer their current unaesthetic situation rather than improving their appearance.

In addition, due to the nature of the rubber from which elastic rubber bands are made, their force weakens over time, and as a result, the elastic rubber bands have to be replaced periodically.

The elastic rubber bands also cause food accumulation therebetween, and as a result, it is characterized by halitosis.

It is an object of the present invention to provide a solution to the above-mentioned and other problems of the prior art.

Other objects and advantages of the invention will become apparent as the description proceeds.

SUMMARY OF THE INVENTION

In one aspect, the present invention is directed to an orthodontic bracket (12), comprising: a vertical bore (32); a bendable drop-in hook (34) threaded into the vertical bore (32); and an annular magnetic object (30), in which the drop-in hook (34) is threaded into.

In another aspect, the present invention is directed to an orthodontic braces arrangement, comprising: at least two distant brackets (12), each installed on a different jaw of a user; and each of the distant brackets (12) having at least one annular magnetic object (30) secured thereto by a bendable drop-in hook; wherein a distance between magnetic objects of one bracket and another bracket is less than 2 mm; thereby providing intermaxillary attraction or propulsion force, depending on a polarity orientation of the magnetic objects.

According to one embodiment of the invention, the magnetic object (30) is in the form of a ring or cylinder.

Preferably, the magnetic object is coated with non-toxic and non-rusting material, such as zinc, gold, titanium and silicon.

Preferably, the magnetic object provides a detaching power of at least 170 gr; the length of the ring or cylinder being about 3 mm; the outer diameter of the ring or cylinder is about 3 mm; and the inner diameter of the ring is about 1 mm.

Preferably, the magnetic object comprises neodymium.

A drop-in hook may be connected either to a top side of the bracket or to a lower side of the bracket. In this way, distant magnetic objects may approach each other at when being in an "effective distance", i.e., at which their attraction or propulsion power is "meaningful" to the orthodontic care, such as at least 100 gr.

The reference numbers have been used to point out elements in the embodiments described and illustrated herein, in order to facilitate the understanding of the invention. They are meant to be merely illustrative, and not limiting. Also, the foregoing embodiments of the invention have been described and illustrated in conjunction with systems and methods thereof, which are meant to be merely illustrative, and not limiting.

BRIEF DESCRIPTION OF DRAWINGS

Preferred embodiments, features, aspects and advantages of the present invention are described herein in conjunction with the following drawings.

It should be understood that the drawings are not necessarily drawn to scale.

DESCRIPTION OF EMBODIMENTS

The present invention will be understood from the following detailed description of preferred embodiments ("best mode"), which are meant to be descriptive and not limiting. For the sake of brevity, some well-known features, methods, systems, procedures, components, circuits, and so on, are not described in detail.

The present invention uses magnetic objects as substitute to the elastic rubber bands 20 of the prior art. According to the present invention, one or more magnetic objects are threaded on a drop-in hook of a bracket. The magnetic objects threaded on the drop-in hook of one bracket operate in conjunction with the magnetic objects threaded on a drop-in hook of another bracket. Assuming the polarity of the magnetic objects of one bracket is the same, the power generated by the magnetic objects may be of attraction or propulsion, depending on the polarity of the magnetic objects.

Figure 3:
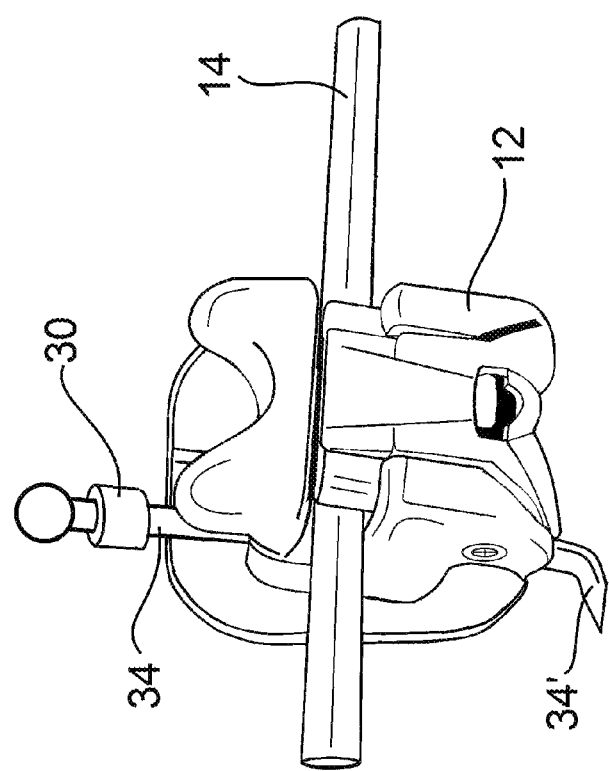
FIG. 3 schematically illustrates an orthodontic bracket, according to one embodiment of the invention.

FIG. 3 schematically illustrates an orthodontic bracket, according to one embodiment of the invention.

The point that characterizes the present invention from the prior art is the annular magnetic object 30, through which the drop-in hook 34 is threaded. The magnetic object 30 is in the form of a ring or cylinder.

Although the length and diameter of the magnetic object 30 (in a ring or cylinder form) may be less than 1 mm, it provides an attraction power which is adequate to substitute the elastic rubber bands, as described herein.

The term "detaching power" is known in the art as the power required for detaching a magnetic object from a ferromagnetic object.

The proposed magnetic objects 30 of the present invention provide a detaching power of 120 gr, which is about 4.28 oz. Hooking two magnetic objects 30 on a single drop-in hook 34 increases the detaching power about 40%. Adding additional magnetic objects increases the magnetic power further.

The proposed magnetic ring/cylinder of the present invention is a neodymium magnet. More particularly, it is made from an alloy of neodymium, iron and boron to form the Nd2Fe14B tetragonal crystalline structure. Presently, neodymium magnets provide a maximum magnetic power per mass in comparison to other magnets, such as ferrite magnets.

In order to decrease corrosion and oxidation of the magnetic objects 30, they can be coated by zinc or other non-toxic material which does not peel "easily", such as gold, silicon and titanium.

In comparison, the common elastic rubber band used in the prior art for orthodontic purposes is stretched to about 25 mm and provides a power of 6 oz, which is about 170 gr (1 oz or ounce equal to 28 gr).

Figure 1:
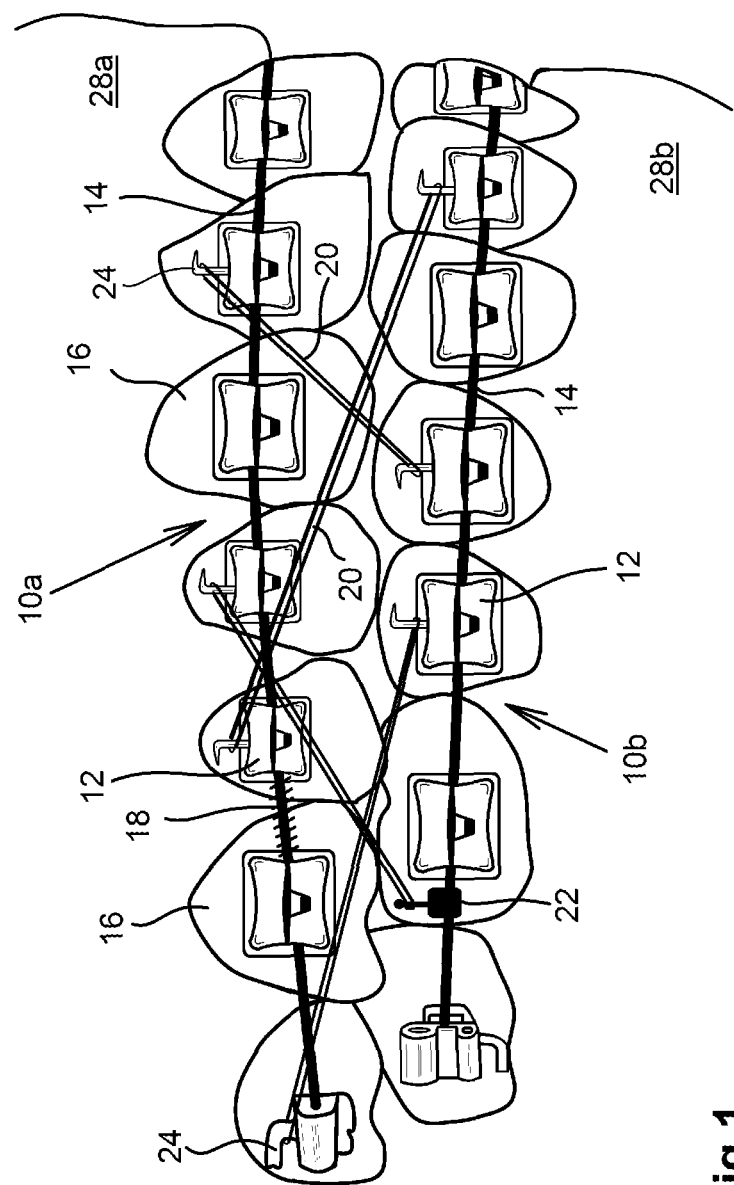
FIG. 1 pictorially illustrates orthodontic braces, according to the prior art.

As illustrated in FIG. 1, due to the required attraction power of an elastic rubber band, the elastic rubber band is not hooked to adjacent teeth, which results in an obstacle for the chewing process of the user thereof.

In contrast to the required length of about 25 mm of an elastic rubber band, the magnetic objects have to be quite close, as the magnetic power of a magnetic object decreases exponentially. Actually, at a distance of 2.5 mm the magnetic power between two magnetic rings is negligible.

On the one hand, this characteristic presents an obstacle to using magnetic objects as a substitute for elastic rubber bands, but on the other hand, the fact that two distant magnets do not attract each other is a benefit when planning orthodontic braces, as the influence of the distant magnets does not have to be taken into consideration.

Figure 4:
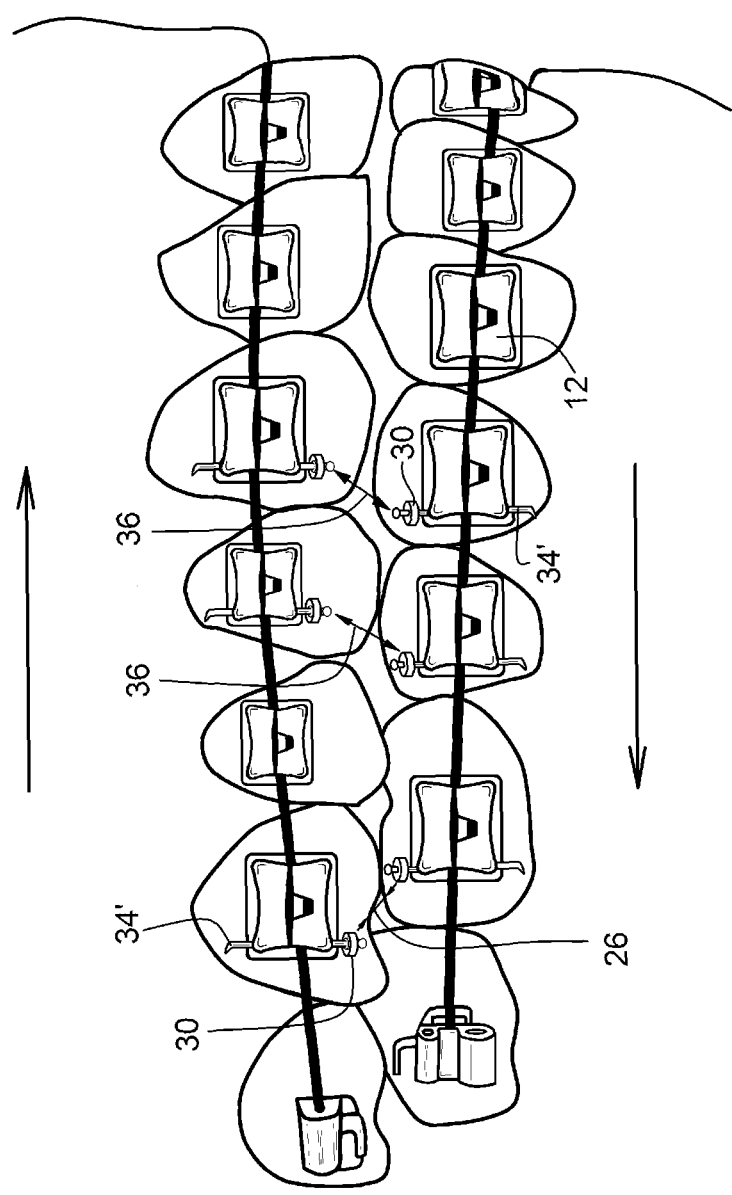
FIG. 4 schematically illustrates orthodontic braces, according to another embodiment of the invention.
Figure 5:
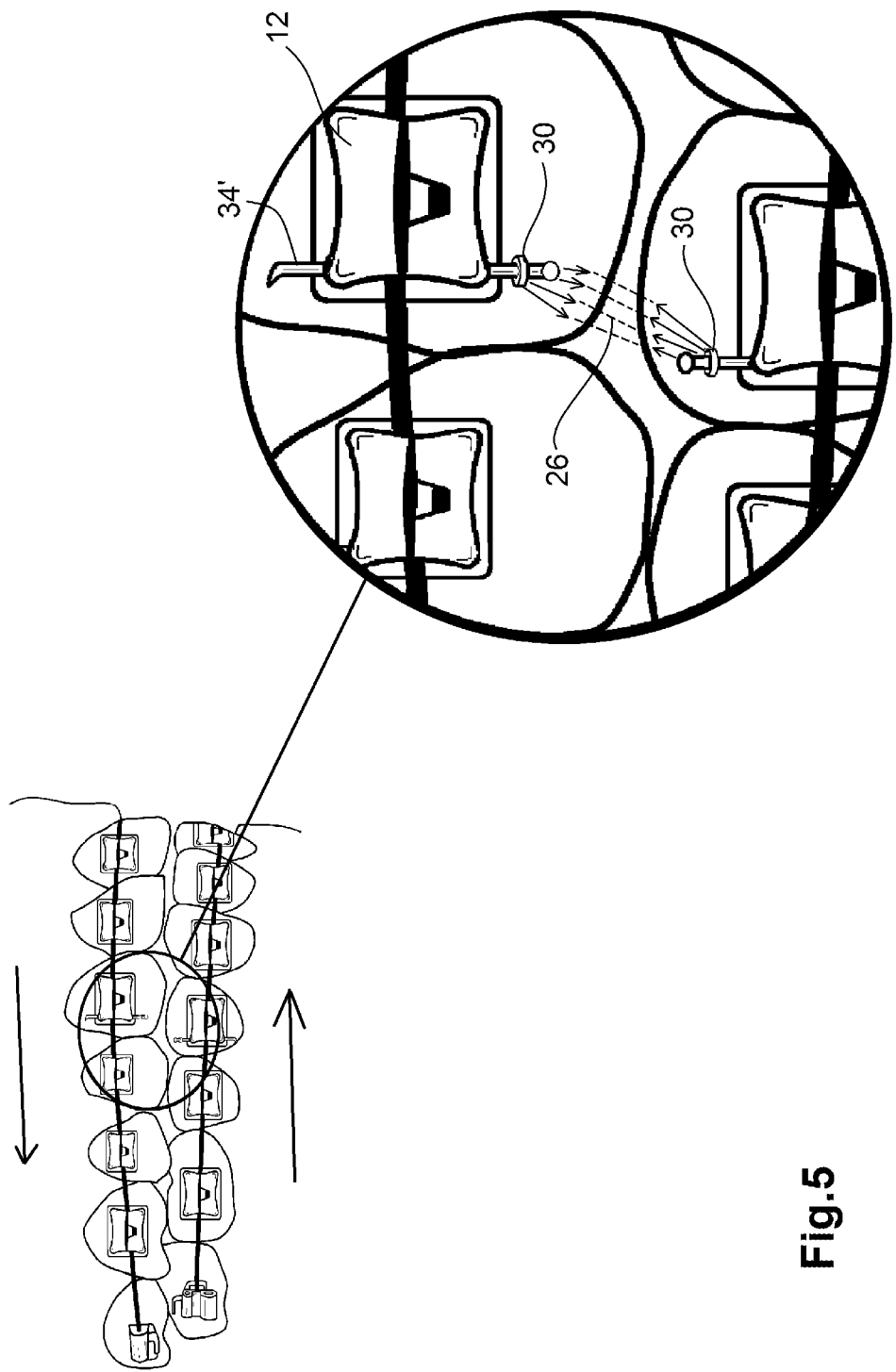
FIG. 5 is a zoomed view of the orthodontic braces illustrated therein, according to one embodiment of the invention.

FIG. 4 schematically illustrates orthodontic braces, according to one embodiment of the invention, and FIG. 5 is a zoomed view of a part thereof.

As illustrated, some of the brackets 12 comprise a drop-in hook 34 connected thereto; on each is threaded a magnetic object 30.

Reference numeral 36 denotes a propulsion force, while reference numeral 26 denotes an attraction force.

As a result of the illustrated orientation of magnetic objects in the orthodontic braces, the teeth of the upper jaw are attracted to the right (according to the figure orientation), while the teeth of the lower jaw are attracted to the left (according to the figure orientation).

Thus, the embodiment illustrated in this figure implements (a) a plurality of magnetic objects 30, and (b) attraction and propulsion power, as a substitute to the elastic rubber bands of the prior art.

FIG. 5 is a zoomed view of a part thereof of orthodontic braces, according to one embodiment of the invention.

Figure 6:
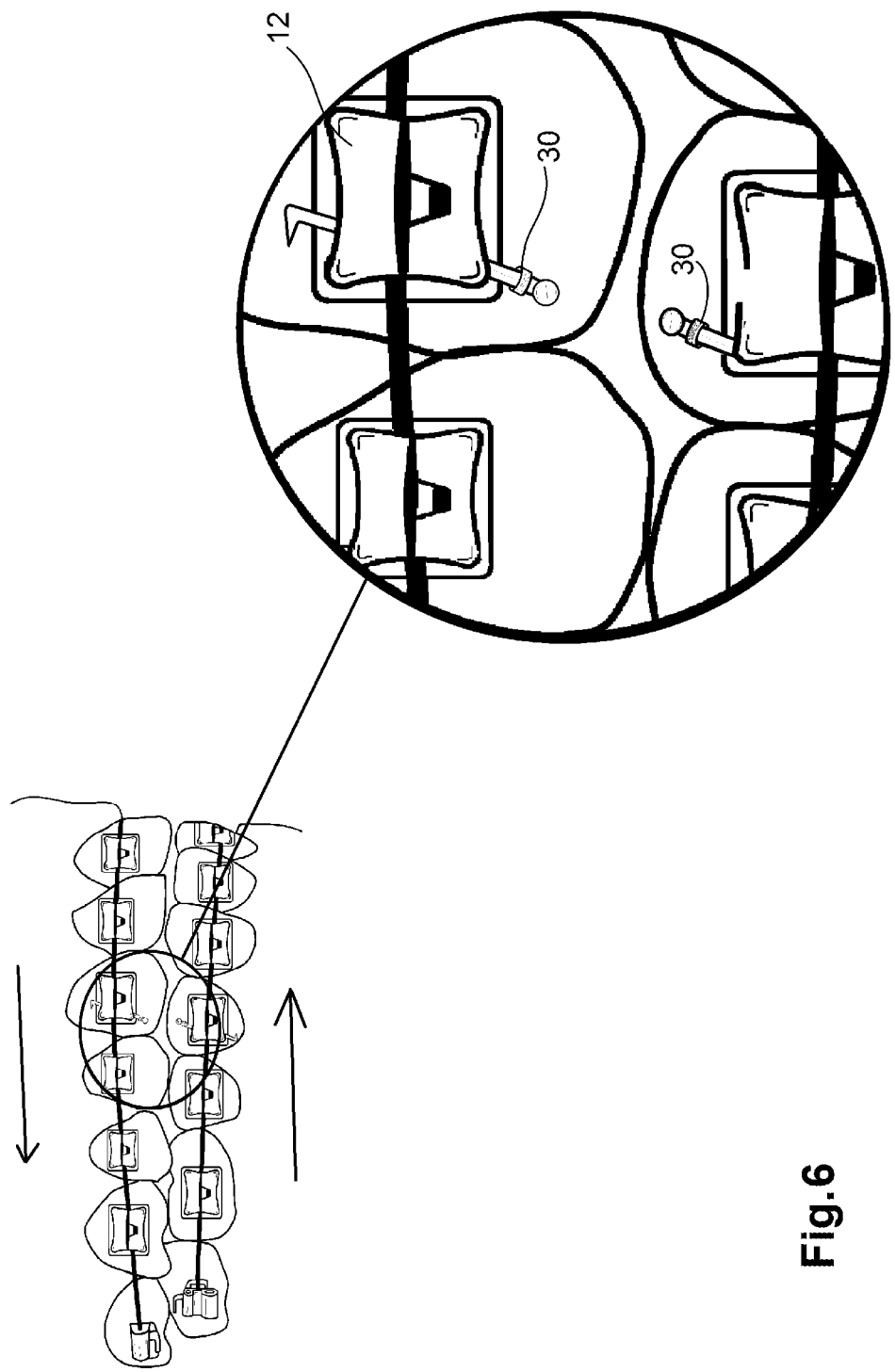
FIG. 6 is a zoomed view of the orthodontic braces illustrated therein, according to another embodiment of the invention.

FIG. 6 is a zoomed view of a part thereof of orthodontic braces, according to another embodiment of the invention.

The difference between the embodiment of FIG. 5 and FIG. 6 is that while the drop-in hooks 34 of FIG. 5 are vertical, the drop-in hooks of FIG. 6 are bent such that the propulsion/attraction power of the magnetic objects 30 is the highest possible using these magnetic objects.

As mentioned above, the use of magnetic objects is preferable in comparison to elastic rubber bands, as it is more comfortable to a user thereof and more aesthetic. In addition, while a decrease in power of a an elastic rubber band over time is meaningful and therefore the elastic rubber band has to be replaced, the attraction power of a magnetic object in such a period is negligible, and therefore does not have to be replaced. In addition, due to the minor dimensions of the proposed magnetic objects, they accumulate less food remnants in comparison to an elastic rubber band.

The present invention allows approaching distant magnetic elements to each other at an "effective distance" (i.e., wherein the distant magnetic objects apply attraction or propulsion force on each other) by the use of drop-in hooks which approach the magnetic objects to each other.

In the figures and/or description herein, the following reference numerals (Reference Signs List) have been mentioned:

numeral 10*a* denotes the wire brace of an upper jaw;
numeral 10*b* denotes the wire brace of a lower jaw;
numeral 12 denotes a bracket;
numeral 14 denotes an arch wire;
numeral 16 denotes tooth/teeth of a user;
numeral 18 denotes a spring;
numeral 20 denotes an elastic rubber band (e.g., made of rubber);
numeral 22 denotes an arch wire hook ("crimpable hook");
numeral 24 denotes a bracket hook;
numeral 26 denotes an attraction (pulling) force;
numeral 28*a* denotes the gingiva of the upper jaw (mandible);
numeral 28*b* denotes the gingiva of the lower jaw (maxilla);
numeral 30 denotes a magnetic object (of which a ring or cylinder is an example thereof);
numeral 32 denotes a vertical bore of a bracket 12;
numeral 34 denotes a drop-in hook (e.g., a pin having a bulb or any other anchoring means at one end thereof); and
numeral 36 denotes a propulsion (pushing) force;

COMPARISON WITH THE CLOSEST PRIOR ART

The following references are considered by the Applicant as the closest prior art:
U.S. Pat. No. 4,565,526(A) to Kawata et al.;
U.S. Pat. No. 4,869,667(A) to Vardimon; and
Abraham M. Blechman. Magnetic force systems in orthodontics—Clinical results of a pilot study. Am J Orthod, March 1985, 201-210.

It discloses an orthodontic appliance for correcting teeth in a user's mouth, which has a bracket having a slot or groove and adapted to be secured to a tooth of the user by means of an adhesive, a correcting wire placed in the slot or groove of the bracket, a magnet body having at least one magnet element, and a holder detachably attached to the bracket for holding the magnet body.

In order to allow attaching a magnetic object to the bracket, Kawata suggests changing the form of the bracket, as illustrated inter alia in FIG. 1 element 11, which is referred in Kawata as "magnet base".

The form of the magnetic assembly disclosed by Kawata comprises a holder 4 to which a connected two magnetic objects 4a and 4b, one from each size thereof. Kawata determines the size of the magnetic objects to be 1 to 3 mm (Kawata, c. 3 ln. 57-59). Thus, the length of a magnetic assembly is larger than the length of the bracket to which it is attached, as can be clearly seen from the figures of the publication.

Ligature wire 12 of Kawata which attaches the correcting wire 7 (i.e., to the arch wire 7) attaches also the holder 4 of Kawata to the bracket. Thus, using Kawata's technology still requires a use of elastic bands.

But, the most significant drawback of Kawata is that as a result of the magnets orientation as seen inter alia in FIG. 10 of Kawata, the disclosed technology of Kawata is adequate to displace adjacent teeth of the same jaw, but not the teeth of one jaw with reference to the teeth of the other jaw.

In contrast to Kawata, the present invention does not need to change the form of a bracket. In addition, the use of drop-in hooks enables to approach distant magnetic objects to each other, until the propulsion or attraction power is "meaningful", e.g., at least 100 gr.

Figure 2:
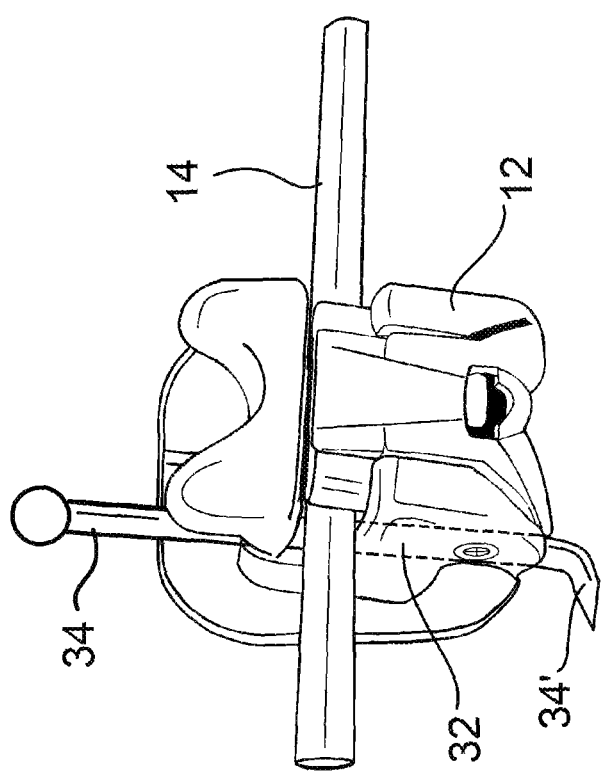
FIG. 2 schematically illustrates an additional anchoring element of the prior art.

Kawata et al. teaches on a magnet (3a, 3b) attached to an orthodontic bracket. Vardimon discloses an orthodontic arch wire (36) having a quadratic profile which passes through the orthodontic brackets, as illustrated in FIGS. 2 and 4 of Vardimon. However, this device (34) connects to the arch wire (36) and not to the orthodontic bracket, in contrast to the present invention. Blechman discloses an intermaxillary orthodontics magnetic system. However, the magnetic elements are also connected to the orthodontic arch wire.

As such, no one of the above mentioned publications, alone or in combination with the others, teaches on an orthodontic bracket having a vertical bore in which is disposed a drop-in-hook which anchors thereto an annular magnet.

In comparison to the above mentioned publications, the present invention allows easy attaching and removal of the magnetic elements to a bracket, without removing the arch wire or the bracket to which the magnetic element is attached.

Additionally, in comparison to Vardimon and Blechman, the elements of the present invention cannot touch the gums of a patient, and therefore do not cause necrosis.

Furthermore, in these publications removing the magnetic elements is complicated, and requires either dismantling the arch wire or the bracket to which the magnetic element is attached.

In contrast to these publications, in the present invention allows easy installation and removal of the magnetic elements, without removing the arch wire or the brackets.

The foregoing description and illustrations of the embodiments of the invention has been presented for the purposes of illustration. It is not intended to be exhaustive or to limit the invention to the above description in any form.

Any term that has been defined above and used in the claims, should to be interpreted according to this definition.

The reference numbers in the claims are not a part of the claims, but rather used for facilitating the reading thereof. These reference numbers should not be interpreted as limiting the claims in any form.

The invention claimed is:
1. An orthodontic bracket (12), comprising:
 a vertical bore (32);
 a bendable drop-in hook (34) threaded into said vertical bore (32); and
 an annular magnetic object (30), in which said drop-in hook (34) is threaded into.
2. An orthodontic bracket (12) according to claim 1, wherein said magnetic object (30) is in a form of a ring or cylinder.

3. An orthodontic bracket (12) according to claim 2, wherein a length of said ring or cylinder is 3 mm with a deviation tolerance of 1.5 mm.

4. An orthodontic bracket (12) according to claim 2, wherein an outer diameter of said ring or cylinder is 3 mm with a deviation tolerance of 1.5 mm.

5. An orthodontic bracket (12) according to claim 2, wherein the inner diameter of said ring or cylinder is 1 mm with a deviation tolerance of 0.5 mm.

6. An orthodontic bracket (12) according to claim 1, wherein said magnetic object is coated with non-toxic and non-rusting material.

7. An orthodontic bracket (12) according to claim 6, wherein said material comprises zinc, silicon, gold or titanium.

8. An orthodontic bracket (12) according to claim 1, wherein said magnetic object provides a detaching power of at least 170 gr.

9. An orthodontic bracket (12) according to claim 1, wherein said magnetic object comprises neodymium.

10. An orthodontic bracket (12) according to claim 1, wherein said drop-in hook is connected to an upper side of said bracket.

11. An orthodontic bracket (12) according to claim 1, wherein said drop-in hook is connected to a bottom side of said bracket.

12. An orthodontic braces arrangement, comprising:
at least two distant brackets (12), each adapted to be installed on a different jaw of a user; and
each of said distant brackets (12) having at least one annular magnetic object (30) secured thereto by a bendable drop-in hook;
wherein a distance between magnetic objects of one bracket and another bracket is less than 2 mm;
thereby providing intermaxillary attraction or propulsion force, depending on a polarity orientation of the magnetic objects.

13. An arrangement according to claim 12, wherein said at least one magnetic object (30) is in a form of a ring or cylinder.

14. An arrangement according to claim 13, wherein a length of said ring or cylinder is 1 mm with a deviation tolerance of 0.5 mm.

15. An arrangement according to claim 13, wherein an outer diameter of said ring or cylinder is 3 mm a deviation tolerance of 1.5 mm.

16. An arrangement according to claim 13, wherein an inner diameter of said ring or cylinder is 1 mm with a deviation tolerance of 0.5 mm.

17. An arrangement according to claim 12, wherein said at least one magnetic object is coated with non-toxic and non-rusting material.

18. An arrangement according to claim 17, wherein said material comprises zinc, silicon, gold or titanium.

19. An arrangement according to claim 12, wherein said at least one magnetic object provides a detaching power of at least 170 gr.

20. An arrangement according to claim 12, wherein said at least one magnetic object comprises neodymium.

* * * * *